United States Patent [19]

Slifkin

[11] Patent Number: 4,666,699

[45] Date of Patent: May 19, 1987

[54] STAIN-FIXATIVE COMPOSITION FOR ENTERIC PARASITES

[75] Inventor: Malcolm Slifkin, Pittsburgh, Pa.

[73] Assignee: Allegheny-Singer Research Institute, Pittsburgh, Pa.

[21] Appl. No.: 708,168

[22] Filed: Mar. 4, 1985

[51] Int. Cl.$^4$ .................. G01N 31/00; G01N 33/48
[52] U.S. Cl. ......................................... 424/7.1; 424/3
[58] Field of Search ........................ 424/7.1, 9, 11, 3

[56] References Cited

PUBLICATIONS

M. M. Brooke, D. Sc., "Polyvinyl Alcohol–Fixative as a Preservative and Adhesive for Protozoa in Dysenteric Stools and Other Liquid Materials, 1949, pp. 1554–1560.
R. B. Borrows, "Improved Preparation of Polyvinyl Alcohol–$H_gCl_2$ Fixative used for Fecal Smears," (1967) pp. 93–56 (Wellcome Research Labs).
B. B. Gardner et al., "Comparison of Direct Wet Mount and Trichrome Staining Techniques for Detecting Entamoeba Species Trophozoites in Stools," (1980), vol. 12, No. 5, pp. 656–658.
L. Shore Garcia et al., "Diagnostic Parasitology Clinical Laboratory Manual," (1975), Chap. 5, pp. 16–20.
W. B. Wheatly, "A Rapid Staining Procedure for Intestinal Amoebae and Flagellates" (1951), pp. 990–991.
J. H. Rampey, Jr., "Modified DMSO–Trichrome Technic for Staining Intestinal Protozoa in Fresh Fecal Smears," (1968), vol. 49, No. 4, p. 611.
D. J. Flournoy et al., "Rapid Trichrome Stain," (1982), Journal of Clinical Microbiology, vol. 16, No. 3, pp. 573–574.
Manual of Clinical Microbiology, 3rd ed., American Society for Microbiology, Washington, D.C. (1980), p. 685.
H. J. Conn's Biological Stains, Ninth ed., R. D. Lillie, M.D. (1977), pp. 165, 639.
McGraw-Hill Encyclopedia of Science and Technology, Parasitology, pp. 628–630, vol. 9.

*Primary Examiner*—Glennon H. Hollrah
*Assistant Examiner*—D. Dinner
*Attorney, Agent, or Firm*—Webb, Burden, Robinson & Webb

[57] ABSTRACT

A stain-fixative composition, for use in the microscopic identification of enteric protozoa and other parasites in fecal specimens, contains Ponceau S Stain, Chlorazol Fast Pink BK Stain, Trypan Blue Stain, dimethyl sulfoxide and a fixative component. The fixative component may be either a polyvinyl alcohol fixative or may be a mixture of isopropanol, acetic acid, liquified phenol, distilled water and optional glutaraldehyde. The stain-fixative composition is simple to prepare, has a long shelf life at ambient conditions, is easy to use and is suitable for preparing formalin or tap water concentrates, wet mount slides, or permanent smears prepared with gelatin-glycerol or resinous mounting media. In addition, the stain-fixative composition is free from the toxic mercury compounds often found in prior art staining reagents. The stain-fixative composition gives superior fixation and resolution, yet its use requires a minimum of time and attention in the laboratory. The method of staining fecal specimens for the identification of enteric parasites is also disclosed.

4 Claims, No Drawings

STAIN-FIXATIVE COMPOSITION FOR ENTERIC PARASITES

INTRODUCTION

In the diagnosis and treatment of gastrointestinal and related diseases, correct identification of enteric protozoa and other parasites is essential. The most widely used method for detecting and identifying gastrointestinal parasites is the microscopic examination of fecal specimens in the diagnostic or hospital laboratory. Ordinarily, this microscopic examination takes place after the specimen has been stained, in order to enable the clinician to differentiate between organisms which, unstained, are impossible to distinguish with accuracy.

The use of a stain during microscopic examination, however, does not alone assure correct identification of enteric organisms; parasites are fragile and can change or deteriorate in the time which elapses before they are examined. As a result, specimens must be examined immediately or must be preserved with a suitable fixative. Because immediate examination of fresh specimens is seldom possible, and because the complex and time-consuming steps required in staining and fixation commensurately delay post-diagnostic treatment, practitioners have endeavored to circumvent these burdensome alternatives by perfecting fixatives and staining procedures which demand as little time and attention as possible.

DESCRIPTION OF THE PRIOR ART

One of the first effective fixatives for protozoa, developed in the 1940's, was the polyvinyl alcohol fixative which is still widely used today. Polyvinyl alcohol (or PVA, the homopolymer of ethenol) is the key agent in a technique wherein a fecal smear is preserved by the adhesive and preservative properties of a polyvinyl alcohol film overlay. As disclosed in "Polyvinyl Alchohol-Fixative as a Preservative and Adhesive for Protozoa in Dysenteric Stools and other Liquid Materials," by M. M. Brooke, D. Sc. and Morris Goldman, M.S., published by the Laboratory Division, Communicable Disease Center, Public Health Service, Federal Security Agency (1949), polyvinyl alcohol fixative became useful for preservation of all vial and smear specimens after the discovery that PVA films are permeable to all commonly employed permanent staining reagents. Certain improvements were made to the PVA-fixative by the incorporation of additional ingredients, as disclosed in "Improved Preparation of Polyvinyl Alcohol-HgCl₂ Fixative used for Fecal Smears," by Robert B. Burrows, the Wellcome Research Laboratories, Burroughs Wellcome & Co., Tuckahoe, NY (1967).

Concommitant with appropriate fixation of specimens, diagnostic parasitology traditionally required the use of one of the two most reliable (and the most complicated) laboratory staining procedures, the trichrome stain and the iron-hemmatoxylin stain. For example, the trichrome stain was pronounced more reliable than the direct wet mount examination method in "Comparison of Direct Wet Mount and Trichrome Staining Techniques for Detecting Entamoeba species trophozoites in Stools," by Becky B. Gardner, Deborah J. Del Junco, Joann Fenn and Jean H. Henegesbaugh, Journal of Clinical Microbiology, Volume 12, No. 5, pp. 656-658 (1980). The trichrome stain and the iron-hematoxylin stain techniques are explained in detail in the Diagnostic Parasitology Clinical Laboratory Manual, by Lynne Shore Garcia and Lawrence R. Ash, The C. V. Mosby Company, St. Louis, MO (1975).

In order to carry out the trichrome staining procedure, fresh or PVA-preserved fecal smears are prepared. The smears are immersed in 70% ethanol for 5 minutes or longer, up to overnight. The smears are then immersed in 70% ethanol to which has been added D'Antoni's iodine and allowed to remain for 2 to 5 minutes. The slide is subsequently immersed in two changes of 70% ethanol, followed by immersion in the trichrome stain; trichrome stain contains Chromotrope 2R, Light Green SF, Phosphotungstic acid, glacial acetic acid and distilled water. (Trichrome stain is purple in color.) The slide is removed from the trichrome stain and immersed in several changes of ethanol, followed by two changes of xylene or toluene. The stained smear is then mounted in a suitable mounting medium and covered with a cover slip or glass.

In order to carry out the iron-hematoxylin staining procedure, fresh or PVA-preserved fecal smears are prepared. The smears are placed in 70% ethanol for 5 minutes or more, up to overnight. The smears are then placed in 70% ethanol to which has been added D'Antoni's iodine, and allowed to remain for 2 to 5 minutes. The smear is then immersed in 70% ethanol and is subsequently washed in running tap water for 10 minutes. The slide is removed to a working solution of iron-hematoxylin (which must be made fresh about every seven days) and allowed to remain for 4 to 5 minutes. The smear is again washed in running tap water for 10 minutes. The smear is washed in several changes of ethanol and two changes of xylene or toluene. The smear is then mounted as for the trichrome stain.

An improvement in the trichrome technique was developed by Wheatley, in which the overall technique was simplified to permit fixation and staining of a fecal smear in about an hour. This improvement is outlined in detail in "A Rapid Staining Procedure for Intestinal Amoebae and Flagellates," by Walter B. Wheatley, Department of Pathology, Lloyd Nolan Hospital, Fairfield, Ala. (1951). A further improvement over the trichrome technique was developed by Rampey, in which dimethyl sulfoxide (DMSO) was sustituted as the fixative, resulting in a staining procedure requiring a total of 11 minutes. The Rampey procedure is set forth in "Modified DMSO-Trichrome Technic for Staining Intestinal Protozoa in Fresh Fecal Smears," by James H. Rampey, Jr., The American Journal of Clinical Pathology, Volume 49, No. 4, The Williams & Wilkins Co. (1968). The trichrome method, unchanged in substance, was further streamlined to the 10 minute procedure as disclosed in "Rapid Trichrome Stain," by D. J. Flournoy, Scott J. N. McNabb, Everett D. Dodd, and Marilynne H. Shaffer, Journal of Clinical Microbiology, Volume 16, No. 3, American Society for Microbiology, pp. 573-574 (1982).

A third technique became available more recently in which the stain and fixative are combined into one solution and staining and fixation of fresh specimens proceed simultaneously. The Chlorazol Black E staining technique, intended for use in identifying protozoa in feces and tissue, is set forth in the Manual of Clinical Microbiology, 3rd ed., American Society for Microbiology, Washington, D.C. (1980) at pp. 685 and 940-941. A basic solution is prepared containing ethyl and methyl alcohol, acetic acid, phenol, phosphotungstic acid and distilled water. To this basic solution is added 5 g./liter Chlorazol Black E dye. The staining technique is carried out by immersing a fresh smear in the Chlorazol Black E basic solution for 2 hours to overnight, taking care that the fresh smear does not dry to any degree between the time of preparation and immersion. The smear is subsequently washed in ethyl alcohol for 15 minutes and treated either with a carbolxylol solution (one part phenol to 2 parts xylol) for 5 minutes or with a sequence of 100% ethyl alcohol and pure xylol followed by mounting in a permanent mounting medium. Unfortunately, the Chlorazol Black E procedure gives good results only with fresh fecal smears, and is less satisfactory when used with PVA-fixed material.

Despite improvements in the speed and simplicity of certain fixation and staining techniques, little or no comparable progress has been made in the development of stains and fixatives which provides high quality resolution and superior fixation along with the benefits of simplified laboratory techniques. Accordingly, a need persists for a simple stain-fixative composition, and a method for using it, which provides superior fixation and staining of fecal specimens yet requires a minimum of time and effort in the laboratory.

SUMMARY OF THE INVENTION

In order to meet this need, the present invention provides a high-resolution stain-fixative composition for fixing and staining enteric parasites which contains Ponceau S Stain, Chlorazol Fast Pink BK Stain, Trypan Blue Stain, dimethyl sulfoxide and a fixative component. The fixative component may be either a polyvinyl alcohol fixative or may be a mixture of isopropanol, acetic acid, liquified phenol, distilled water and optional glutaraldehyde. The stain-fixative composition is simple to prepare, has a shelf life of several months, is easy to use and is suitable for use in the preparation of formalin or tap water parasite concentrates, wet mount fecal specimens or permanent mount fecal smears. In addition, the stain-fixative composition is free from the toxic mercury compounds often found in prior art staining reagents. The stain-fixative composition enables the preparation of fixed specimens demonstrating superior resolution as compared with specimens prepared by prior art procedures, yet requires a minimum of time and attention in the laboratory.

DETAILED DESCRIPTION OF THE INVENTION

The present invention is a stain-fixative composition, for use in the microscopic identification of protozoa and other parasites, which contains Ponceau S, Chlorazol Fast Pink BK and Trypan Blue dyes. The stain-fixative composition also contains dimethyl sulfoxide and a fixative. The fixative may be either a polyvinyl alcohol fixative or an isopropanol fixative. Laboratory preparation of the stain-fixative composition requires only that the various components of the composition be mixed together, yielding a storage stable stain-fixative composition with which a fecal specimen may be stained and fixed in a simple laboratory procedure. Each component of the stain-fixative composition, and its appropriate level in parts by volume, is described in detail below.

Each of the three dyes incorporated into the present composition has a different international color index number and a plurality of synonyms. Ponceau S is also known as C.I. Acid Red 112, Ponceau Red and Ponceau S Extra, all of which have an international color index number of 27195. The chemical formula for Ponceau S is 3-hydroxy-4((2-sulfo-4-((-4-sulfophenyl(azo)phenyl)azo) 2,7 naphthalenedisulfonic acid tetrasodium salt.

The Chlorazol Fast Pink BK dye has a C.I. of 25380 and its chemical formula is 5,5'-(carbonylbis(imino(2-sulfo-4,1-phenylene)azo))bis(6-amino-4-hydroxy) 2-naphthalenesulfonic acid tetrasodium salt. The synonyms for Chlorazol Fast Pink BK are Aizen Primula Pink 2BLH, Aizen Primula Pink 2BLH Special, Amanil Fast Pink 2B, Atlantic Fast Pink 2BL, Belamine Fast Pink, Belamine Fast Pink BK, Calcodur Pink 2BL, Chloramine Fast Pink BK, Chlorantine Fast Pink 2B, Chlorantine Fast Red 2B, Chrome Leather Pink B, Diazol Light Pink 2B, Diphenyl Blue Red B, Diphenyl Fast Pink BF, Diphenyl Fast Pink BK, Direct Fast Pink B, Direct Fast Pink 4BL, Direct Light Pink M 2BL, Eliamina Pink 2BL, Fastusol Pink BBACF, Fastusol Pink BBL, Fenaluz Pink 2B, Helion Pink 2B, Paranol Fast Pink 2BL, Pyrazoline Pink 4BL, Saturn Pink 2B, Sirius Pink 4BL, Sirius Pink BB, Sirius Supra Rubine B, Solantine Pink 4BL, Solar Rubine CB, Solius Pink 2B, Suprazo Pink 2B, Suprexcel Pink BL, Tertrodirect Fast Rose 2B, Triantine Fast Pink B, Triantine Light Pink B, Direct Fast Pink S, Direct Fast Rose S, Direct Lightfast Pink S, Direct Lightfast Rose S, C.I. Direct Red 75, Lightfast Rose S, Diphenyl Pink EBE, Chlorazol Fast Pink, Benzo Fast Pink 2BL and Chlorazol Fast Pink 2BL.

The Trypan Blue Dye has a C.I. of 23850 and its chemical formula is 3,3'-[(3,3'-Dimethyl[1,1'-biphenyl]-4,4'-diyl)bis(azo)]bis[5-amino-4-hydroxy-2,7-naphthalenedisulfonic acid] tetrasodium salt. The synonyms for Trypan Blue are Benzamine Blue, Diamine Blue, Benzo Blue, Congo Blue, Dianil Blue, Naphthylamine Blue and Niagara Blue.

Although each of the three dyes is commercially available in dry form, diagnostic laboratories frequently store various dyes in the convenient Stock Stain form. A Stock Stain is prepared by weighing out the correct amount of dye, grinding the dye in a mortar and pestle, dissolving the dye into an appropriate solution, bottling the solution and, after 4 to 6 weeks, decanting and filtering the supernatant dye into a suitable storage flask. Stock Stains thus prepared do not deteriorate and may be stored at ambient temperature at least for several months. Accordingly, for the purposes of the present application, Stock Chlorazol Fast Pink BK Stain refers to a solution of 1.0% by weight Chlorazol Fast Pink BK dye in distilled water. Similarly, Stock Ponceau S Stain refers to a 0.5% by weight solution of Ponceau S dye in isopropanol fixative. (Isopropanol fixative contains about 1 to 3% by volume acetic acid, about 1 to 3% by volume liquified phenol, about 25 to 35% by volume isopropanol and about 59 to 73% by volume distilled water.) Stock Trypan Blue Stain refers to a 1.0% by weight solution of Trypan Blue dye in isopropanol fixative.

In the formulation of the present stain-fixative composition, these Stains are added to the other components of the composition in amounts which yield superior resolution in the simplified microscopic examination and identification of protozoa and other parasites. Accordingly, in a sample of the stain-fixative composition, about 5 to 10% by volume is Stock Ponceau S Stain, about 5 to 10% by volume is Stock Chlorazol Fast Pink BK Stain, and about 1.5 to 4% by volume is Stock Trypan Blue Stain. The proportionate amounts of each of the three Stains is added, with stirring, to a suitable laboratory vessel chosen for preparation of the stain-fixative composition.

In addition to the three Stains, the stain-fixative composition includes a fixative component. The fixative component may be a polyvinyl alcohol fixative or may be the isopropanol fixative described above. The isopropanol fixative described above may be used as is or may be supplemented with glutaraldehyde. Glutaraldehyde (50% biological grade), alternately known as pentanedial, glutaral, glutane dialdehyde and 1,3-diformylpropane, may be incorporated into the isopropanol fixative in the amount of up to about 20% by volume, replacing an equivalent volume of distilled water and, accordingly, may be present in the amount of up to about 17% by volume of the total stain-fixative composition. The polyvinyl alcohol fixative may be a polyvinyl alcohol fixative composition known in the art, or may be a solution containing about 1 to 6% by volume polyvinyl alcohol, about 0.5 to 4% by volume glycerol, and about 90 to 96.5% by volume isopropanol fixative. The polyvinyl alcohol fixative component has the same diluent and fixative properties as the isopropanol fixative and, therefore, either is incorporated into the composition in the same amount by volume. Accordingly, the fixative component constitutes about 68 to 85% by volume of the stain-fixative composition regardless of which of the two is selected for use.

The present stain-fixative composition also contains a supplemental fixative, dimethyl sulfoxide. Dimethyl sulfoxide, also known as DMSO or sulfinylbismethane, is incorporated into the stain-fixative composition in the amount of about 3 to 8% by volume.

After the various elements of the stain-fixative composition are admixed in a suitable laboratory vessel, the composition is removed to a sterile flask and sealed. The composition may be stored for several months and used as needed.

After the fecal specimen is available for analysis, the laboratory practitioner suspends a small specimen sample in an appropriate amount of stain-fixative, allows the suspended specimen to sediment, and prepares a microscope slide from the sedimented material. More particularly, suspension of the sample is accomplished by adding one part feces to a vial containing four parts stain-fixative and vigorously shaking the capped vial. After thorough agitation, the vial is allowed to remain undisturbed for one-half hour (or longer) at room temperature (between 15° and 30° C.), during which time the fecal specimen settles out of suspension into a fixed, stained sediment. The sediment is then used in the preparation of slides suitable for microscopic examination.

Alternatively, the fecal specimen may be placed directly into the stain-fixative at the time the specimen arrives at the nursing station. Rather than placing the specimen in an empty specimen receptacle, therefore, the hospital worker transfers the specimen to a somewhat larger receptacle containing a quantity of the stain-fixative; the receptacle is then sealed and dispatched to the laboratory as usual. The sealed receptacle should contain both the fecal specimen and about 2 to 4 parts by volume of stain-fixative based on one part fecal specimen. Due to the relatively large volume of feces in the receptacle and due to the impossibility of the same vigorous agitation which is possible with small, capped laboratory vials, the fecal specimen prepared in this manner ordinarily requires one hour or more, at room temperature, for staining and fixation, in contrast with the one-half hour required in the procedure described in the previous paragraph. (One hour is adequate staining and fixing time, however, even if the receptacle is left undisturbed.) The required extra half hour of staining and fixing time usually presents no inconvenience because one-half hour or more frequently elapses during processing, pick-up and delivery of the specimen from the nursing station to the laboratory. More importantly, the technique offers distinct advantages in that little or no effort is required of nursing personnel (pre-filled receptacles may be furnished to each nursing station, for example) and fixation of the specimen begins at the earliest possible moment after specimen collection. Finally, due to its extended contact with the stain-fixative composition and the dispersant action characteristic of any aqueous solution, even a formed specimen will disperse and migrate into a sedimented layer in the bottom of the receptacle. As a result, this alternate procedure results in the same fixed, stained sediment as does the procedure described above.

Suitable microscope slides include wet mount slides and permanent smears. Wet mount slides and permanent smears are very similar microscope slides, differing only in that the permanent smear has been treated to ensure preservation of the prepared slide for weeks or months. The wet mount, however, also offers a beneficial degree of preservation: a wet mount slide prepared directly from the fixed, stained sediment described above will not deteriorate for at least 48 hours after its preparation, providing more than adequate specimen preservation for even the busiest of laboratories.

To prepare a wet mount slide, the preparer removes an aliquot of the fixed, stained sediment described above and places it in a small glass vial or tube. An aliquot of the supernatant is also added to the vial, yielding a mixture of sediment and supernatant which is 25 to 50% by volume supernatant and 50 to 75% by volume sediment. The capped vial or tube is incubated in a 50° to 60° C. waterbath for 10 to 20 minutes, after which it is shaken to resuspend the sedimented fecal material. With a sterile pipette or dropper or other suitable laboratory instrument, two drops of the suspension in the vial are dropped in the center of a sterile microscope slide; a sterile coverslip is drawn over and placed atop the liquid to form a smear. The wet mount slide may be examined under a microscope within 48 hours of preparation, and perhaps later, if the slide is stored away from heat. Wet mount slides are prepared by the same procedure whether or not the stain-fixative contains PVA.

To prepare a permanent smear with stain-fixative containing PVA, the preparer removes an aliquot of the fixed, stained sediment and places it in a glass vial. As with the wet mount procedure, the aliquot should be 25 to 50% by volume supernatant and 50 to 75% by volume sedimented specimen. The vial is capped, incubated in a 50° to 60° C. waterbath for 10 to 20 minutes, and shaken thoroughly. Two drops of the suspension are placed on a sterile microscope slide and smeared with a wooden applicator. The slide is then partially dried by exposing it to ambient air for about two minutes, after which the slide is immersed in isopropanol or 100% ethanol for 10 minutes and then in xylene for 10 minutes. After the addition of a permanent mounting medium such as the synthetic resin dissolved in toluene and sold under the trade name Permount, the smear is ready to be covered with a coverslip and examined under various microscope magnifications.

To prepare a permanent smear with the isopropanol-fixative-containing stain-fixative composition, the practitioner removes aliquots of the fixed stained sediment and the supernatant and places them in a glass vial. As with the permanent smear described above, the vial should contain 25 to 50% by volume supernatant and 50 to 75% by volume sedimented specimen. The vial is capped, incubated and shaken as above. Two drops of the suspension are placed on a sterile microscope slide. A tube of mounting medium containing water, gelatin and glycerol is incubated in a 50° to 60° C. waterbath until fluid. About six drops of the gelatin-glycerol medium are added to and mixed with the suspension on the slide, using a wooden applicator. After the coverslip is placed atop the smear, the slide may be examined at any time and, after 12 hours, the gelatin-glycerol mounting medium will harden to preserve the specimen in a permanent smear. Gelatin-glycerol mounting media contain about 0.01 to 25% glycerol in an aqueous gelatin colloid.

The stain-fixative of the present invention does not overstain protozoa and other parasites and, as a result, does not require destaining techniques of any kind. Although optimal staining and fixing of specimens is achieved in about one-half to about two and one-half hours, specimens may remain immersed or suspended in the stain-fixative for up to about eight hours before any decrease in resolution is perceptible during microscopic examination. In addition, if a specimen has been immersed in stain-fixative for two hours or longer, waterbath incubation of the specimen may be omitted from each of the three preceding procedures: heat is not necessary to complete staining and fixation if the specimen is immersed for two or more hours.

The present stain-fixative composition is well-suited not only to the procedures described above but has additional utility in laboratory procedures which isolate parasites from a fecal specimen by differential centrifugation. These differential centrifugation techniques are known in the art, and may be carried out using the aliquots of incubated supernatant and sediment described above. A small specimen of the isolated parasite phase resulting from differential centrifugation may then be transferred to a slide, prepared as a wet mount or permanent smear, and examined under a microscope.

Because protozoa and other parasites cannot survive, apart from their hosts, for any significant period of time, laboratory equipment is seldom if ever contaminated with parasites. Accordingly, although the use of sterile laboratory equipment is preferred, the pipettes, applicators, slides and other equipment used in the present method need not be sterilized. The use of sterile laboratory equipment does, however, guard against the introduction of unsuspected contaminants into the procedures outlined above.

The invention will be more fully described with reference to the specific examples herein set forth.

EXAMPLE I

A basic fixative was prepared containing 300 ml. isopropanol, 20 ml. acetic acid, 20 ml. liquified phenol and 660 ml. distilled water. The fixative was mixed at high speed with a high-speed magnetic stirring device. After mixing was complete, 1.5 ml. 50% Biological Grade glutaraldehyde was added to 12.0 ml. of the mixture and the resulting stain-fixative was stirred with a stirring rod.

The stain-fixative composition was prepared by admixing the 13.5 mls. of basic fixative, 0.9 ml. dimethyl sulfoxide, 0.45 ml. Stock Trypan Blue Stain, 1.2 ml. Stock Chlorazol Fast Pink BK Stain and 1.2 ml. Stock Ponceau S Stain. The admixture was transferred to a vial and a 5 ml. portion of a fecal specimen was added to the vial. The capped vial was shaken thoroughly. The vial was left undisturbed at room temperature for one-half hour, after which time the fecal specimen settled into a fixed, stained sediment.

A wet mount slide of the fixed, stained sediment was prepared by removing a 0.5 ml. aliqot of the sediment and a 0.25 ml. aliquot of the supernatant and placing the aliquots in a small glass tube. The tube was capped and incubated in a 56° C. waterbath for 15 minutes. The tube was shaken to resuspend the fecal material. Two drops of the resuspended fecal material were removed to a microscope slide with a pipette, a coverslip was added, and the slide was labelled and stored for 12 hours. After storage, the slide was examined for parasites by conventional binocular microscopy.

A permanent smear of the fixed, stained sediment was prepared by removing a 0.75 ml. aliquot of the sediment and a 0.25 ml. aliquot of the supernatant and placing the aliquots in a small glass tube. The tube was capped, incubated at 56° C. for 10 minutes, and shaken to resuspend the sediment. Two drops of the resuspended material were placed on a microscope slide and smeared with a wooden applicator. The smeared specimen was covered with 7 drops of a permanent mounting medium, containing gelatin and glycerol, which had been liquified by incubation at 56° C. for 8 minutes. The mounting medium and the smeared specimen were mixed well with a wooden applicator stick and covered with a cover slip. The prepared slide was examined immediately and again after 1 week; no changes in the trophozoite or cyst protozoa appeared between immediate examination and the 1-week follow-up, and color resolution did not deteriorate.

EXAMPLE II

A basic fixative was prepared containing 300 ml. isopropanol, 20 ml. acetic acid, 20 ml. liquified phenol, and 600 ml. distilled water. The fixative was mixed at high speed. To 200 ml. of this basic fixative were added 20 g. polyvinyl alcohol (particulate) and 6.0 ml. glycerol, with stirring. The admixture was heated in a 90° C. waterbath for 3 minutes to dissolve the polyvinyl alcohol. The admixture was stirred, cooled and diluted with another 200 ml. of the basic fixative solution. The resultant polyvinyl fixative composition was removed to clean laboratory flask and sealed for storage.

The stain-fixative composition was prepared by admixing 13.5 ml. of the polyvinyl fixative composition with 0.9 ml. dimethyl sulfoxide, 0.45 ml. Stock Trypan Blue Stain, 1.2 ml. Stock Chlorazol Fast Pink BK Stain and 1.2 ml. Stock Ponceau S Stain. The admixture was transferred to a vial and a 5 ml. portion of a fecal specimen was added to the vial. The capped vial was shaken thoroughly. The vial was left undisturbed at room temperature for one-half hour, after which time the fecal specimen settled into a fixed, stained sediment.

A wet mount slide of the fixed, stained sediment was prepared by removing a 0.5 ml. aliquot of the sediment and a 0.25 ml. aliquot of the supernatant and placing the aliquots in a small glass tube. The tube was capped and incubated in a 56° C. waterbath for 15 minutes. The tube was shaken to resuspend the fecal material. Two drops of the resuspended fecal material were removed to a microscope slide with a pipette, a coverslip was added, and the slide was labelled and examined.

A permanent smear of the fixed, stained sediment was prepared by removing a 0.75 ml. aliquot of the sediment and a 0.25 ml. aliquot of the supernatant and placing the aliquots in a small glass tube. The tube was capped, incubated at 56° C. for 10 minutes, and shaken to resuspend the sediment. Two drops of the resuspended material were placed on a microscope slide and smeared with a wooden applicator. The slide was dried for two minutes at ambient conditions (20° C., 40% humidity). The slide was subsequently immersed in 100% ethanol for 10 minutes, followed by immersion in xylene for 10 minutes. Eight drops of synthetic resin permanent mounting medium were deposited over the smear and a coverslip was positioned atop the mounting medium before the resin began to harden. The slide was examined for parasites by conventional binocular microscopy.

EXAMPLE III

The stain-fixative composition was prepared and used to fix and stain a 5 ml. portion of a fecal specimen in accordance with Example II. Two ml. of the fixed, stained sediment were removed from the bottom of the vial and placed in a 15 ml. conical-base centrifuge tube. The 2 ml. sample was 60% sediment and 40% supernatant. The tube was filled with tap water approximately to the half-capacity mark and gently stirred with a wooden stirring rod. Tap water was added to the three-fourth mark and the contents of the tube were stirred with the same stirring rod. The tube was placed in a centrifuge opposite a tube filled to the three-fourth mark with tap water, and the two tubes were centrifuged at 1500 rpm for 2 minutes. The supernatant was decanted and the sediment was resuspended in tap water and ethyl acetate by filling the tube to the half-capacity mark with water and filling the tube to the three-fourth mark with ethyl acetate (about 3 ml.). The tube was stoppered and shaken vigorously. The tube was again centrifuged, opposite a blank, at 1500 rpm for 2 minutes. The tube was removed from the centrifuge without agitation and examined for differential layering. Four layers resulted from the centrifugation: a top layer of ethyl acetate, a second layer of fecal debris, a lower layer of water and a bottom sediment of most of the parasites from the fecal specimen sample. The fecal debris was removed with a wooden applicator stick and the ethyl acetate and water were decanted with a pipette. A few drops of water were allowed to remain in the centrifuge tube and the parasite layer was resuspended therein.

A wet mount slide of the resuspended parasite layer was prepared by removing two drops of the resuspended parasites from the centrifuge tube with a pipette, placing the drops on a clean microscope slide and covering with a coverslip. A permanent smear of the resuspended parasite layer was prepared in accordance with the permanent smear procedure outlined in Example II. Both the wet mount and permanent smears were examined under a binocular microscope.

EXAMPLE IV

A fixed, stained sediment was prepared in accordance with Example I. Two ml. of the fixed, stained sediment were removed from the bottom of the vial and prepared in accordance with the differential centrifugation techniques of Example III, except that formalin was substituted for the tap water. Both wet mount slides and permanent smears were prepared, and the slides were examined for trophozoite and cyst protozoa and other parasites.

I claim:

1. The method of staining and fixing a fecal specimen, consisting essentially of:
   preparing a fixative by combining about 1 to 3% by volume acetic acid, about 1 to 3% by volume liquified phenol, about 25 to 35% by volume isopropanol, about 39 to 73% by volume water and up to about 20% by volume of a 50% aqueous solution of glutaraldehyde;
   admixing 68 to 85% by volume of the fixative with 5 to 10% by volume Stock Ponceau S Stain, 5 to 10% by volume Stock Chlorazol Fast Pink BK Stain, 1.5 to 4% by volume Stock Trypan Blue Stain, and 3 to 8% by volume dimethyl sulfoxide;
   fixing and staining a fecal specimen by suspending the specimen in the admixture;
   sedimenting the specimen; and
   magnifying and examining the specimen for enteric parasites.

2. The method of staining and fixing a fecal specimen, consisting essentially of:
   preparing a fixative by combining about 0.9 to 2.8% by volume acetic acid, about 0.9 to 2.8% by volume liquified phenol, about 22.5 to 33% by volume isopropanol, about 53 to 70% by volume water, about 1 to 6% by volume polyvinyl alcohol and about 0.5 to 4% by volume glycerol;
   admixing 68 to 85% by volume of the fixative with 5 to 10% by volume Stock Ponceau S Stain, 5 to 10% by volume Stock Chlorazol Fast Pink BK Stain, 1.5 to 4% by volume Stock Trypan Blue stain, and 3 to 8% by volume dimethyl sulfoxide;
   fixing and staining a fecal specimen by suspending the specimen in the admixture;
   sedimenting the specimen; and
   magnifying and examining the specimen for enteric parasites.

3. A stain-fixative composition for fixing and staining enteric parasites, comprising:
   about 5 to 10% by volume Stock Ponceau S stain;
   about 5 to 10% by volume Stock Chlorazol Fast Pink BK Stain;
   about 1.5 to 4% by volume Stock Trypan Blue Stain;
   about 3 to 8% by volume dimethyl sulfoxide; and
   about 68 to 85% by volume of a fixative, which fixative comprises about 1 to 3% by volume liquified phenol, about 25 to 35% by volume isopropanol, up to about 20% by volume glutaraldehyde and about 39 to 73% by volume water.

4. A stain-fixative composition for fixing and staining enteric parasites, comprising:
   about 5 to 10% by volume Stock Ponceau S Stain;
   about 5 to 10% by volume Stock Chlorazol Fast Pink BK Stain;
   about 1.5 to 4% by volume Stock Trypan Blue Stain;
   about 3 to 8% by volume dimethyl sulfoxide; and
   about 68 to 85% by volume of a fixative, which fixative comprises about 0.9 to 2.8% by volume acetic acid, about 0.9 to 2.8% by volume liquified phenol, about 22.5 to 33% by volume isopropanol, about 53 to 75% by volume water, about 1 to 6% by volume polyvinyl alcohol and about 0.5 to 4% by volume glycerol.

* * * * *